United States Patent
Sugitani

(10) Patent No.: US 9,156,780 B2
(45) Date of Patent: Oct. 13, 2015

(54) SULFONIC ACID GROUP-CONTAINING DIAMINE COMPOUND AND METHOD FOR PRODUCING THE SAME

(75) Inventor: Tooru Sugitani, Osaka (JP)

(73) Assignee: Nitto Denko Corporation, Osaka (JP)

( * ) Notice: Subject to any disclaimer, the term of this patent is extended or adjusted under 35 U.S.C. 154(b) by 76 days.

(21) Appl. No.: 13/823,518

(22) PCT Filed: Mar. 12, 2012

(86) PCT No.: PCT/JP2012/001697
§ 371 (c)(1),
(2), (4) Date: Mar. 14, 2013

(87) PCT Pub. No.: WO2012/132269
PCT Pub. Date: Oct. 4, 2012

(65) Prior Publication Data
US 2013/0178649 A1    Jul. 11, 2013

(30) Foreign Application Priority Data

Mar. 28, 2011    (JP) ................................. 2011-069685

(51) Int. Cl.
*C07C 309/38* (2006.01)
*C07C 309/50* (2006.01)
*C07C 309/43* (2006.01)
*C07C 303/20* (2006.01)

(52) U.S. Cl.
CPC ............. *C07C 309/50* (2013.01); *C07C 303/20* (2013.01); *C07C 309/43* (2013.01); *C07C 2103/18* (2013.01)

(58) Field of Classification Search
CPC ........................... C07C 13/567; C07C 309/38
USPC .......................................................... 562/71
See application file for complete search history.

(56) References Cited

U.S. PATENT DOCUMENTS

| 4,797,427 | A | 1/1989 | Sanders et al. |
| 6,861,560 | B2 * | 3/2005 | Walter et al. .................. 564/330 |
| 8,158,441 | B2 | 4/2012 | Cecillon et al. |
| 2011/0144373 | A1 | 6/2011 | Swan et al. |

FOREIGN PATENT DOCUMENTS

| JP | 63-275557 | 11/1988 |
| JP | 3-017084 | 1/1991 |
| JP | 2003-068326 | 3/2003 |
| JP | 2004-026831 | 1/2004 |
| JP | 2007-523899 | 8/2007 |
| JP | 2009-501922 | 1/2009 |
| WO | 2005/077899 | 8/2005 |

* cited by examiner

*Primary Examiner* — Yong Chu
*Assistant Examiner* — Sonya Wright
(74) *Attorney, Agent, or Firm* — Hamre, Schumann, Mueller & Larson, P.C.

(57) ABSTRACT

The present invention provides a novel sulfonic acid group-containing diamine compound represented by formula (1) below, and a method for producing the same. This compound has a fluorene skeleton with sulfonic acid groups or derivatives thereof. In this compound, a substituent having an amino group is bonded to each of carbon atoms at the 2-position and the 7-position in the skeleton, and no substituent is bonded to a carbon atom at the 9-position in the skeleton. A in formula (1) denotes an optionally-substituted divalent aliphatic group (having a carbon number of 10 or less) or an optionally-substituted divalent aromatic group (having the number of rings of 4 or less), for example.

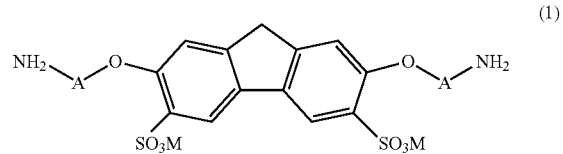

(1)

2 Claims, 2 Drawing Sheets

SULFONIC ACID GROUP-CONTAINING DIAMINE COMPOUND AND METHOD FOR PRODUCING THE SAME

TECHNICAL FIELD

The present invention relates to a novel sulfonic acid group-containing diamine compound having amino groups and a fluorene skeleton with sulfonic acid groups, and to a method for producing the compound.

BACKGROUND ART

Diamine compounds having sulfonic acid groups or derivatives of sulfonic acid group (sulfonic acid group-containing diamine compounds) are widely used as a crosslinking agent or a raw material for thermosetting polymers or polycondensation polymers such as polyamide, polyimide, epoxy resin, and polyurethane. Fluorene has a fused ring structure composed of three rings, and has a high planarity of the molecular structure. Polymers formed using a sulfonic acid group-containing diamine compound having a fluorene skeleton as a raw material or a crosslinking agent are expected to have properties derived from the high planarity of the fluorene skeleton.

The carbon atom located at the 9-position in the fluorene skeleton is a carbon atom of methylene group, and it thus has a higher reactivity compared to other carbon atoms in the skeleton. Therefore, conventionally, a number of sulfonic acid group-containing diamine compounds (see Patent Literature 1) in which a substituent having an amino group is bonded to the carbon atom at the 9-position in the skeleton, such as 9,9-bis(3,5-dimethyl-4-aminophenyl)fluorene-2,7-disulfonic acid, 9,9-bis(3-methoxy-4-aminophenyl)fluorene-2,7-disulfonic acid, and 9,9-bis(3-fluoro-4-aminophenyl)fluorene-2,7-disulfonic acid, are synthesized and commercially available. Hereinafter, the 1 to 9-positions in the fluorene skeleton may be abbreviated simply as "the 1-position" to "the 9-position", respectively, by omitting the phrase "in the fluorene skeleton".

CITATION LIST

Patent Literature

Patent Literature 1: JP 2003-68326 A

SUMMARY OF INVENTION

Technical Problem

It is an object of the present invention to provide a novel sulfonic acid group-containing diamine compound having a fluorene skeleton with sulfonic acid groups or derivatives thereof, in which a substituent having an amino group is bonded to each of the carbon atoms at the 2-position and the 7-position in the skeleton, with no substituent being bonded to the carbon atom at the 9-position in the skeleton.

It is also an object of the present invention to provide a production method that allows efficient synthesis of such a novel sulfonic acid group-containing diamine compound.

Solution to Problem

The sulfonic acid group-containing diamine compound of the present invention is a compound represented by formula (1) below.

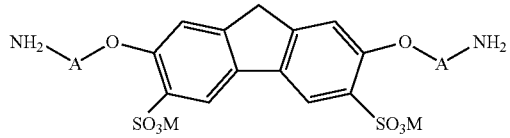

In formula (1), the group represented by [—$SO_3M$] is a sulfonic acid group, a salt of sulfonic acid group, or an ester of sulfonic acid group, A in the partial structure represented by [—O-A-$NH_2$] is: a divalent aliphatic group $R^1$ which may have a substituent and has a carbon number of 1 to 10; a divalent aromatic group $Ar^1$ which has 1 to 4 ring structures and may have a substituent; a group represented by formula: [—$Ar^2$—$Z^1$—$Ar^3$—] (where $Ar^2$ and $Ar^3$, which may be the same as or different from each other, each are a divalent aromatic group which has 1 to 4 ring structures and may have a substituent, and $Z^1$ is a direct bond (—), an ether group (—O—), a thioether group (—S—), or a sulfone group (—$SO_2$—)); a group represented by formula: [—$R^2$—$Ar^4$—] (where $R^2$ is a divalent aliphatic group which may have a substituent and has a carbon number of 1 to 10, and $Ar^4$ is a divalent aromatic group which has 1 to 4 ring structures and may have a substituent); or a group represented by formula: [—$Ar^5$—$R^3$—$Ar^6$—] (where $Ar^5$ and $Ar^6$, which may be the same as or different from each other, each are a divalent aromatic group which has 1 to 4 ring structures and may have a substituent, and $R^3$ is a divalent aliphatic group which may have a substituent and has a carbon number of 1 to 10). The substituent which the aliphatic groups $R^1$, $R^2$, and $R^3$, and the aromatic groups $Ar^1$, $Ar^2$, $Ar^3$, $Ar^4$, $Ar^5$, and $Ar^6$ may have is at least one selected from a methyl group, an ethyl group, a propyl group, a butyl group, a trifluoromethyl group, a phenyl group, a phenoxy group, a phenylthio group, and a benzenesulfonyl group.

The method for producing the sulfonic acid group-containing diamine compound of the present invention is a method for producing the above-mentioned sulfonic acid group-containing diamine compound of the present invention represented by formula (1). The method includes: a step of obtaining a compound <b> represented by formula (4) by a condensation reaction of 2,7-dihydroxy-9-fluorenone represented by formula (2) and a compound <a> represented by formula (3):

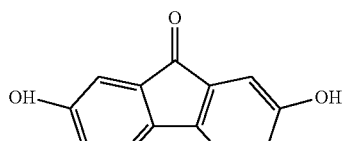

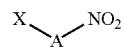

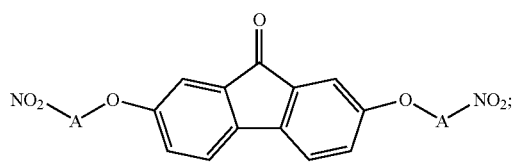

a step of obtaining a compound <c> represented by formula (5) by reducing a ketone group at the 9-position in the fluorene skeleton of the compound <b> to a state where a hydroxy group is bonded to the carbon atom at the 9-position, and thereafter acetylating the hydroxy group:

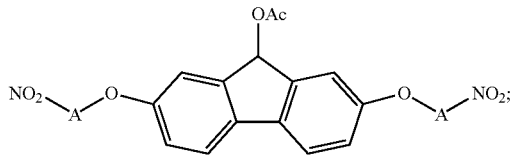

(5)

a step of obtaining a diamine compound <d> represented by formula (6) by reducing the carbon atom at the 9-position, to which the acetoxy group is bonded, in the fluorene skeleton of the compound <c> and reducing nitro groups that are included in the substituents derived from the compound <a> and bonded to the carbon atoms at the 2-position and the 7-position in the skeleton:

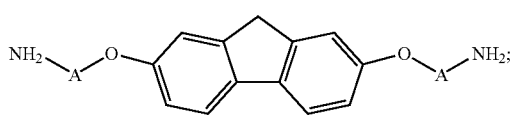

(6)

and a step of obtaining a sulfonic acid group-containing diamine compound represented by formula (1) in which sulfonic acid groups or derivatives thereof are introduced to carbon atoms (the carbon atoms at the 3-position and the 6-position) on the aromatic rings in the fluorene skeleton by subjecting the compound <d> to a sulfonation reaction:

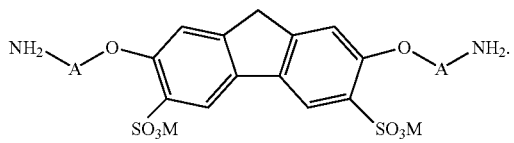

(1)

X in formula (3) is a halogen group. A in formulae (3) to (6) is as described above for A in formula (1), that is, the same group as A in the partial structure represented by [—O-A-NH$_2$] of the sulfonic acid group-containing diamine compound represented by the formula (1).

Advantageous Effects of Invention

According to the present invention, a novel sulfonic acid group-containing diamine compound having a fluorene skeleton with sulfonic acid groups or derivatives thereof, in which a substituent having an amino group is bonded to each of the carbon atoms at the 2-position and the 7-position in the skeleton, with no substituent being bonded to the carbon atom at the 9-position in the skeleton is obtained.

According to the present invention, it is also possible to synthesize such a novel sulfonic acid group-containing diamine compound efficiently.

DESCRIPTION OF EMBODIMENTS

Sulfonic Acid Group-Containing Diamine Compound

Figure 1:
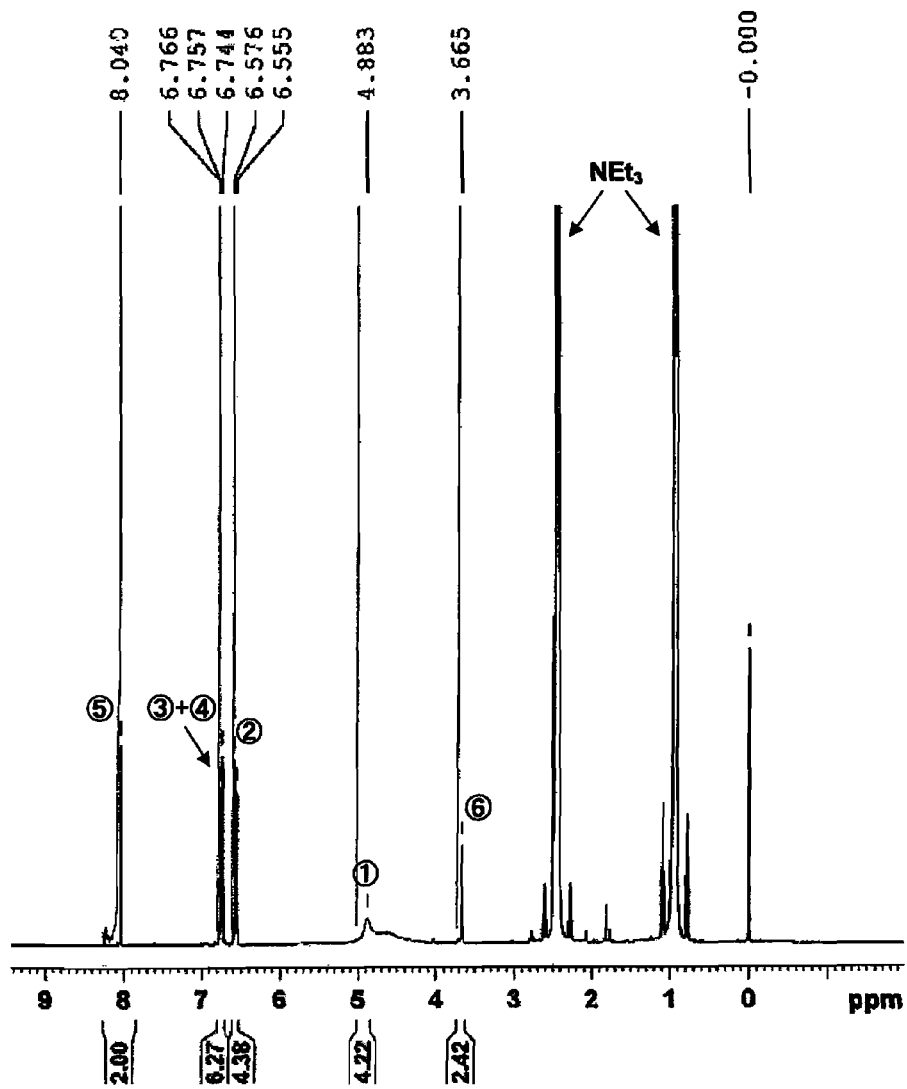
FIG. 1 is a graph showing a result of the proton nuclear magnetic resonance spectroscopy ($^1$H-NMR) of 2,7-bis(4-aminophenoxy)fluorene-3,6-disulfonic acid synthesized in the example.

The sulfonic acid group-containing diamine compound of the present invention is a compound represented by formula (1) below.

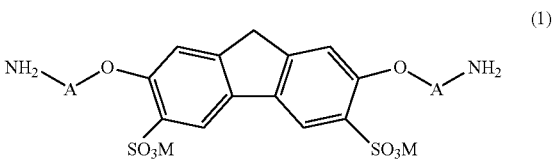

(1)

A in formula (1) is as described above. The group represented by [—SO$_3$M] in formula (1) denotes a sulfonic acid group or a derivative thereof. The derivative of sulfonic acid group, for example, is a salt of sulfonic acid group or an ester of sulfonic acid group (sulfonic acid ester group). In the case where the group represented by [—SO$_3$M] is a sulfonic acid group, M is a hydrogen atom (H). In the case where this group is a salt of sulfonic acid group, M is a metal atom or a protonated amine compound. When M is a metal atom, this group is a metal salt of sulfonic acid group. When M is the above-mentioned amine compound, this group is an amine salt of sulfonic acid group. The metal atom, for example, is an alkali metal atom or an alkaline earth metal atom. In the case where the group is an ester of sulfonic acid group, M is an alkyl group, particularly, an alkyl group having a carbon number of 1 to 4.

It is difficult, for example, for a polycondensation polymer which has been obtained using a conventional sulfonic acid group-containing diamine compound that has a fluorene skeleton in which a substituent having an amino group is bonded to the carbon atom at the 9-position to exhibit properties derived from the high planarity of the skeleton because the fluorene skeleton is oriented perpendicular to the polymer main chain. Further, the planarity of the fluorene skeleton itself is lost when a substituent is bonded to the carbon atom at the 9-position. On the other hand, the sulfonic acid group-containing diamine compound, represented by formula (1), of the present invention has a fluorene skeleton with sulfonic acid groups or derivatives thereof, in which a substituent having an amino group is bonded to each of the carbon atoms at the 2-position and the 7-position in the skeleton. Further, no substituent is bonded to the carbon atom at the 9-position in the skeleton. According to the sulfonic acid group-containing diamine compound of the present invention with such a molecular structure, polymers (such as polycondensation polymers or thermosetting polymers) having properties derived from the high planarity of the fluorene skeleton, for example, are expected to be formed.

The sulfonic acid group-containing diamine compound of the present invention, for example, is a compound represented by formulae (7), (8), (9), (10), or (11) below.

(7)
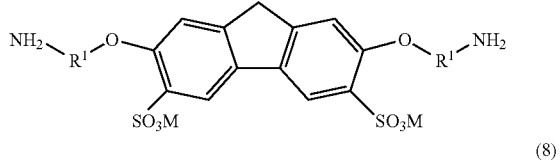

(8)
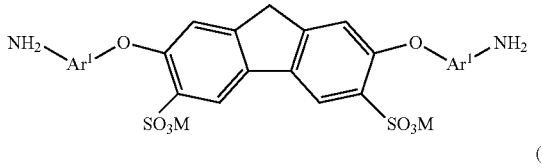

(9)
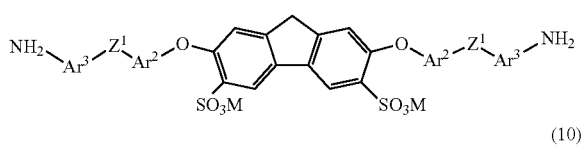

(10)
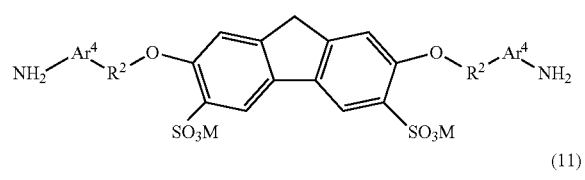

(11)
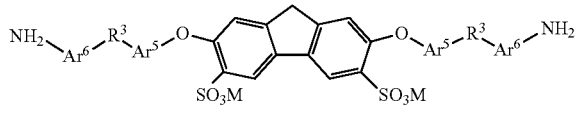

$R^1$, $R^2$, and $R^3$ in formulae (7), (10), and (11) each are a divalent aliphatic group which may have a substituent and has a carbon number of 1 to 10. $Ar^1$, $Ar^2$, $Ar^3$, $Ar^4$, $Ar^5$, and $Ar^6$ in formulae (8) to (11) each independently denote a divalent aromatic group which has 1 to 4 ring structures and may have a substituent. The substituent which the aliphatic groups $R^1$, $R^2$, and $R^3$, and the aromatic groups $Ar^1$, $Ar^2$, $Ar^3$, $Ar^4$, $Ar^5$, and $Ar^6$ may have is at least one selected from a methyl group, an ethyl group, a propyl group, a butyl group, a trifluoromethyl group, a phenyl group, a phenoxy group, a phenylthio group, and a benzenesulfonyl group.

$Z^1$ in formula (9) is a direct bond (–), an ether group (—O—), a thioether group (—S—), or a sulfone group (—SO$_2$—).

The group represented by [—SO$_3$M] in formulae (7) to (11) is the same as the group represented by [—SO$_3$M] in formula (1), that is, a sulfonic acid group or a derivative thereof. Specifically, this group is a sulfonic acid group, a salt of sulfonic acid group, or an ester of sulfonic acid group. The salt of sulfonic acid group, for example, is a metal salt of sulfonic acid group or an amine salt of sulfonic acid group. The metal in the metal salt of sulfonic acid group, for example, is alkali metal or alkaline earth metal.

The divalent aliphatic groups $R^1$, $R^2$, and $R^3$ in formulae (1), (7), (10), and (11) each are preferably a divalent saturated aliphatic group. The divalent saturated aliphatic group, for example, is a methylene group, an ethylene group, or a propylene group, and is preferably a methylene group or an ethylene group. As mentioned above, these divalent aliphatic groups $R^1$, $R^2$, and $R^3$ may have one or more substituents.

In the case where the divalent aromatic groups $Ar^1$, $Ar^2$, $Ar^3$, $Ar^4$, $Ar^5$, and $Ar^6$ in formulae (1) and (8) to (11) have a plurality (2 to 4) of ring structures, the plurality of ring structures preferably form a fused ring. The divalent aromatic groups $Ar^1$, $Ar^2$, $Ar^3$, $Ar^4$, $Ar^5$, and $Ar^6$ each, for example, are a phenylene group, a naphthylene group (naphthalenediyl group), a phenanthrenediyl group, a pyrenediyl group, or a fluorenediyl group, and are preferably a phenylene group or a naphthylene group. Such an aromatic group includes a heteroaromatic group. As mentioned above, these divalent aromatic groups $Ar^1$, $Ar^2$, $Ar^3$, $Ar^4$, $Ar^5$, and $Ar^6$ each may have one or more substituents.

$Z^1$ in formulae (1) and (9) is preferably an ether group (—O—).

In the sulfonic acid group-containing diamine compound of the present invention, A in formula (1) is preferably the aliphatic group $R^1$ or the aromatic group $Ar^1$, more preferably the aromatic group $Ar^1$.

The sulfonic acid group-containing diamine compound represented by formula (7), for example, is 2,7-bis(aminomethoxy)fluorene-3,6-disulfonic acid,
2,7-bis(aminoethoxy)fluorene-3,6-disulfonic acid,
2,7-bis(3-aminopropoxy)fluorene-3,6-disulfonic acid,
2,7-bis(2-aminopropoxy)fluorene-3,6-disulfonic acid,
2,7-bis(4-aminobutoxy)fluorene-3,6-disulfonic acid,
2,7-bis(3-aminobutoxy)fluorene-3,6-disulfonic acid,
2,7-bis(2-aminobutoxy)fluorene-3,6-disulfonic acid,
2,7-bis(5-aminopentoxy)fluorene-3,6-disulfonic acid,
2,7-bis(4-aminopentoxy)fluorene-3,6-disulfonic acid,
2,7-bis(3-aminopentoxy)fluorene-3,6-disulfonic acid,
2,7-bis(2-aminopentoxy)fluorene-3,6-disulfonic acid,
2,7-bis(6-aminohexyloxy)fluorene-3,6-disulfonic acid,
2,7-bis(5-aminohexyloxy)fluorene-3,6-disulfonic acid,
2,7-bis(4-aminohexyloxy)fluorene-3,6-disulfonic acid,
2,7-bis(3-aminohexyloxy)fluorene-3,6-disulfonic acid,
2,7-bis(2-aminohexyloxy)fluorene-3,6-disulfonic acid,
2,7-bis(1-amino-1-phenylmethoxy)fluorene-3,6-disulfonic acid,
2,7-bis(2-amino-2-phenyl-ethoxy)fluorene-3,6-disulfonic acid,
2,7-bis(2-amino-2-phenoxy-ethoxy)fluorene-3,6-disulfonic acid,
2,7-bis(2-amino-2-phenylsulfanyl-ethoxy)fluorene-3,6-disulfonic acid,
2,7-bis(2-amino-2-benzenesulfonyl-ethoxy)fluorene-3,6-disulfonic acid,
2,7-bis(3-amino-2-phenyl-propoxy)fluorene-3,6-disulfonic acid,
2,7-bis(3-amino-2-phenoxy-propoxy)fluorene-3,6-disulfonic acid,
2,7-bis(3-amino-2-phenylsulfanyl-propoxy)fluorene-3,6-disulfonic acid,
2,7-bis(3-amino-2-benzene sulfonyl-propoxy)fluorene-3,6-disulfonic acid,
2,7-bis(4-amino-2-phenyl-butoxy)fluorene-3,6-disulfonic acid,
2,7-bis(4-amino-2-phenoxy-butoxy)fluorene-3,6-disulfonic acid,
2,7-bis(4-amino-2-phenylsulfanyl-butoxy)fluorene-3,6-disulfonic acid,
2,7-bis(4-amino-2-benzenesulfonyl-butoxy)fluorene-3,6-disulfonic acid,
2,7-bis(4-amino-3-phenyl-butoxy)fluorene-3,6-disulfonic acid,
2,7-bis(4-amino-3-phenoxy-butoxy)fluorene-3,6-disulfonic acid,
2,7-bis(4-amino-3-phenylsulfanyl-butoxy)fluorene-3,6-disulfonic acid,
2,7-bis(4-amino-3-benzenesulfonyl-butoxy)fluorene-3,6-disulfonic acid, 2,7-bis(5-amino-3-phenyl-pentoxy)fluorene-3,6-disulfonic acid,
2,7-bis(5-amino-3-phenoxy-pentoxy)fluorene-3,6-disulfonic acid,
2,7-bis(5-amino-3-phenylsulfanyl-pentoxy)fluorene-3,6-disulfonic acid, or
2,7-bis(5-amino-3-benzenesulfonyl-pentoxy)fluorene-3,6-disulfonic acid.

The sulfonic acid group-containing diamine compound represented by formula (8), for example, is 2,7-bis(4-aminophenoxy)fluorene-3,6-disulfonic acid,
2,7-bis(3-aminophenoxy)fluorene-3,6-disulfonic acid,
2,7-bis(2-aminophenoxy)fluorene-3,6-disulfonic acid,
2,7-bis(5-amino-1-naphthoxy)fluorene-3,6-disulfonic acid,
2,7-bis(8-amino-1-naphthoxy)fluorene-3,6-disulfonic acid,
2,7-bis(3-amino-2-naphthoxy)fluorene-3,6-disulfonic acid,
2,7-bis(8-amino-2-naphthoxy)fluorene-3,6-disulfonic acid,
2,7-bis(4-amino-1-naphthoxy)fluorene-3,6-disulfonic acid,
2,7-bis(2-amino-1-naphthoxy)fluorene-3,6-disulfonic acid,
2,7-bis(6-amino-2-naphthoxy)fluorene-3,6-disulfonic acid,
2,7-bis(7-amino-2-naphthoxy)fluorene-3,6-disulfonic acid,
2,7-bis(6-amino-1-pyrenoxy)fluorene-3,6-disulfonic acid,
2,7-bis(8-amino-1-pyrenoxy)fluorene-3,6-disulfonic acid,
2,7-bis(3-amino-1-pyrenoxy)fluorene-3,6-disulfonic acid,
2,7-bis(10-amino-9-phenanthrenoxy)fluorene-3,6-disulfonic acid,
2,7-bis(7-amino-2-fluorenoxy)fluorene-3,6-disulfonic acid,
2,7-bis(8-amino-3-phenanthridineoxy)fluorene-3,6-disulfonic acid,
2,7-bis(3-amino-8-phenanthridineoxy)fluorene-3,6-disulfonic acid,
2,7-bis(8-amino-6-phenyl-3-phenanthridineoxy)fluorene-3,6-disulfonic acid, or
2,7-bis(3-amino-6-phenyl-8-phenanthridineoxy)fluorene-3,6-disulfonic acid.

The sulfonic acid group-containing diamine compound represented by formula (9), for example, is 2,7-bis(4'-amino-4-biphenyloxy)fluorene-3,6-disulfonic acid, 2,7-bis(4'-amino-3,3'-dimethyl-4-biphenyloxy)fluorene-3,6-disulfonic acid,
2,7-bis[4-(4-aminophenoxy)phenoxy]fluorene-3,6-disulfonic acid,
2,7-bis[4-(4-aminophenylsulfanyl)phenoxy]fluorene-3,6-disulfonic acid, or
2,7-bis[4-(4-aminobenzenesulfonyl)phenoxyl]fluorene-3,6-disulfonic acid.

The sulfonic acid group-containing diamine compound represented by formula (10), for example, is
2,7-bis[1-(4-aminophenyl)methoxy]fluorene-3,6-disulfonic acid,
2,7-bis[1-(3-aminophenyl)methoxy]fluorene-3,6-disulfonic acid, or
2,7-bis[1-(2-aminophenyl)methoxy]fluorene-3,6-disulfonic acid.

The sulfonic acid group-containing diamine compound represented by formula (11), for example, is 2,7-bis{4-[1-(4-aminophenyl)-2,2,2-trifluoro-1-trifluoromethylethyl]phenoxy}fluorene-3,6-disulfonic acid.

In the sulfonic acid group-containing diamine compound of the present invention, a substituent having an amino group is bonded to each of the carbon atoms at the 2-position and the 7-position via an ether bond (—O—). The ether bond provides excellent rotatability for the molecular chains. Thus, it is expected that the use of a polymer formed using the sulfonic acid group-containing diamine compound of the present invention allows a film, for example, having high bending properties and high flexibility to be produced.

The sulfonic acid group-containing diamine compound of the present invention can be used in the same applications as conventional diamine compounds. Examples of such applications include a crosslinking agent or a raw material for polycondensation polymers or thermosetting polymers such as polyamide, polyimide, epoxy resin, and polyurethane.

In the case where the group represented by [—SO$_3$M] in the sulfonic acid group-containing diamine compound of the present invention is a sulfonic acid group, the handling can be facilitated by protecting the sulfonic acid group. It is possible to protect the sulfonic acid group, for example, by converting the sulfonic acid group into an ester of sulfonic acid group, a metal salt of sulfonic acid group, or an amine salt of sulfonic acid group. The protected sulfonic acid group can be converted again into a sulfonic acid group easily by hydrolysis, ion exchange, etc.

The sulfonic acid group-containing diamine compound of the present invention, for example, can be produced by the method for producing the sulfonic acid group-containing diamine compound of the present invention. The sulfonic acid group-containing diamine compound of the present invention can be produced also by another production method, but the production method of the present invention enables efficient production of such compound.

<Production Method of Sulfonic Acid Group-Containing Diamine Compound>

In the sulfonic acid group-containing diamine compound of the present invention, no substituent is bonded to the carbon atom at the 9-position in the fluorene skeleton. In conventional methods, however, a number of by-products in which a substituent is bonded to the carbon atom at the 9-position are generated because of the high reactivity of the carbon atom at the 9-position in the fluorene skeleton. Therefore, not only great efforts are required for purification of the desired sulfonic acid group-containing diamine compound, but also the yield rate of such compound is significantly reduced. In addition, the synthesis of the sulfonic acid group-containing diamine compound with no substituent bonded to the carbon atom at the 9-position is even impossible, depending on the method.

As a result of studies on the production method of such a sulfonic acid group-containing diamine compound, the inventors have found that the formation of by-products in which a substituent is bonded to the carbon atom at the 9-position is suppressed and efficient synthesis of the sulfonic acid group-containing diamine compound of the present invention can be achieved by: [1] using, as a starting material, 2,7-dihydroxy-9-fluorenone in which the carbon atom at the 9-position in the fluorene skeleton forms a ketone group (>C=O) (that is, the 9-position in the fluorene skeleton is a ketone group) and a hydroxy group is bonded to each of the carbon atoms at the 2-position and the 7-position; [2] introducing a substituent having a nitro group to each of the 2-position and the 7-position through a condensation reaction with the hydroxy group, while preventing binding of a substituent to the carbon atom at the 9-position by protecting this carbon atom with the ketone group; [3] reducing the carbon atom at the 9-position to a state where a hydroxy group is bonded thereto and thereafter once acetylating the hydroxy group to form an acetoxy group (—OAc); [4] reducing, to amino groups, the nitro groups included in substituents that are bonded to the carbon atoms at the 2-position and the 7-position, as well as reducing, to a methylene group (—CH$_2$—), the carbon atom at the 9-position to which the acetoxy group is bonded; and [5] introducing sulfonic acid groups or derivatives thereof to aromatic rings in the fluorene skeleton by a sulfonation reaction.

That is, in the method for producing the sulfonic acid group-containing diamine compound of the present invention, the sulfonic acid group-containing diamine compound of the present invention can be produced efficiently by: using 2,7-dihydroxy-9-fluorenone having a fluorene skeleton as a starting material; introducing a nitro group-containing substituent to each of the carbon atoms at the 2-position and the 7-position by means of a condensation reaction of a hydroxy group; preventing binding of a substituent to the carbon atom at the 9-position during the introduction by protecting this carbon atom with a ketone group; changing the ketone group at the 9-position, through a state where a hydroxy group is bonded to the carbon atom, to a state where an acetoxy group is bonded to the carbon atom, so as to allow reduction to a methylene group in the subsequent step; reducing the nitro groups in the nitro group-containing substituents to amino groups as well as performing the above-mentioned reduction to a methylene group; and introducing sulfonic acid groups or derivatives thereof to aromatic rings in the fluorene skeleton by a sulfonation reaction.

Hereinafter, each step is specifically described.

In the method for producing the sulfonic acid group-containing diamine compound of the present invention, 2,7-dihydroxy-9-fluorenone represented by formula (2) and the compound <a> represented by formula (3) are subjected to condensation to allow the compound <b> represented by formula (4) to be obtained (Reaction 1).

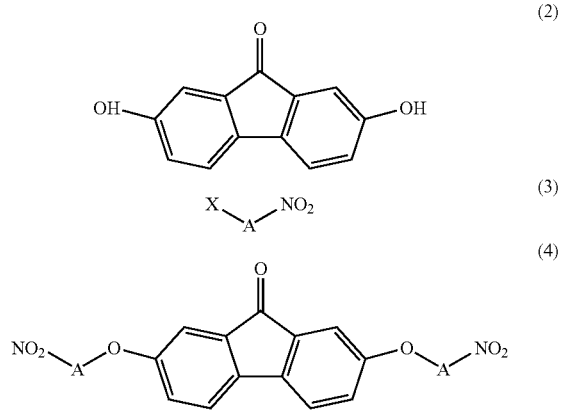

X in the compound <a> represented by formula (3) is a halogen group. The type of halogen that forms such a group is F, Cl, Br, or I, preferably F, Cl, or Br, more preferably F or Cl. The types of A in the compounds <a> and <b> represented by formulae (3) and (4), and the types of A in the compounds represented by formulae (4) to (6) below each are as described above for A in the sulfonic acid group-containing diamine compound represented by formula (1). A in formula (3) is the same as A in formula (1), as long as the molecular structure does not change through the intermediate reactions. A in the compound <a> represented by formula (3) may be selected depending on the substituents having amino groups in the target diamine compound. For example, when the target diamine compound is expressed by formula (1), it may be the same as A in formula (1).

Typical examples of A in formula (3) include a phenylene group, a naphthalenediyl group, a methylene group, and an ethylene group.

Reaction 1 is a dehydrohalogenation condensation reaction and an etherification reaction between the hydroxy group in 2,7-dihydroxy-9-fluorenone and the compound <a>. Reaction 1 proceeds efficiently in the presence of a basic catalyst.

The basic catalyst, for example, is oxides, hydroxides, carbonates, hydrogencarbonates, hydrides, and alkoxides of alkali metals. Specific examples of the basic catalyst include sodium oxide, lithium oxide, potassium hydroxide, sodium hydroxide, lithium hydroxide, potassium carbonate, sodium carbonate, potassium bicarbonate, sodium hydrogencarbonate, sodium hydride, potassium t-butoxide, sodium methoxide, and sodium ethoxide. Two or more types of basic catalysts may be used. The use amount of basic catalyst, for example, is an equivalent mole of 1.0 to 5.0, preferably an equivalent mole of 2.0 to 4.0, with respect to 2,7-dihydroxy-9-fluorenone.

In Reaction 1, the reaction solvent is not specifically limited as long as Reaction 1 proceeds. However, it is preferably a polar aprotic solvent. Specific examples of the reaction solvent include N-methylformamide, N,N-dimethylformamide, N,N-dimethylacetamide, dimethylsulfoxide, dimethylsulfone, sulfolane, N-methyl-2-pyrrolidinone, N-methylpyrrolidone (NMP), 1,3-dimethyl-2-imidazolidinone, N,N,N',N'-tetramethylurea, hexamethylphosphotriamide, 1,3-dimethyl-3,4,5,6-tetrahydro-2(1H)-pyrimidinone, tetrahydrofuran, acetonitrile, and acetone. The use amount of reaction solvent is not specifically limited. However, it is 1 to 20 times by weight the total amount of reactant, for example. The polar aprotic solvent can be used continuously as a reaction solvent in Reactions 2 and 3 after Reaction 1.

In Reaction 1, quaternary ammonium salt, quaternary phosphate, macrocyclic polyethers such as crown ethers, nitrogen-containing macrocyclic polyethers such as cryptands, nitrogen-containing chain polyethers, phase transfer catalysts such as polyethylene glycol and alkyl ethers thereof, copper powder, copper salt, etc., may be used in combination as a reaction accelerator.

In Reaction 1, binding of a substituent to the carbon atom at the 9-position is suppressed due to the use of fluorenone having a ketone group at the 9-position in the fluorene skeleton as a starting material. Thus, the sulfonic acid group-containing diamine compound of the present invention can be efficiently produced through the subsequent Reactions 2 and 3. It was confirmed by the inventors that, when the same reaction as Reaction 1 was conducted using 2,7-dihydroxy-9-fluorene instead of 2,7-dihydroxy-9-fluorenone as a starting material, a substituent was bonded to the carbon atom at the 9-position.

Next, the ketone group at the 9-position of the compound <b> obtained after Reaction 1 is reduced to a state where a hydroxy group is bonded to the carbon atom at the 9-position, and thereafter the hydroxy group is acetylated. Thus, the compound <c> represented by formula (5) is obtained (Reaction 2).

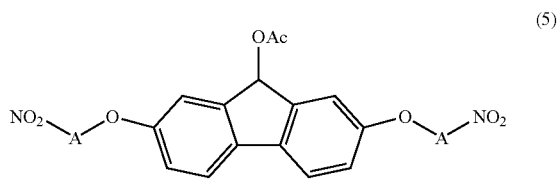

In order to obtain the sulfonic acid group-containing diamine compound of the present invention, the ketone group at the 9-position of the compound <b> is required to be reduced to a methylene group. However, the reduction of the ketone group in the compound <b> does not proceed any further than the state where a hydroxy group is bonded to the carbon atom at the 9-position. Therefore, after the reduction has proceeded to a state where the hydroxy group is bonded to the carbon atom at the 9-position, the hydroxy group is once acetylated to a state where an acetoxy group (—OAc) is bonded thereto. It is not until this state (compound <c>) has been achieved that it becomes possible to reduce the ketone group at the 9-position in the fluorene skeleton to a methylene group.

In Reaction 2, the reduction of the ketone group may be performed, for example, by techniques such as hydrogenation, hydride reduction, and metal reduction. Reductants and/or catalysts to be used in the respective techniques are not specifically limited. For hydrogenation and metal reduction, fine powder of metals such as nickel, copper-chromium oxide, ruthenium, rhodium, and platinum; a catalyst obtained by allowing such fine powder to be adsorbed on an insoluble carrier such as activated carbon, alumina, and diatomite; or a complex of an organic compound and a metal, for example, can be used. For hydride reduction, diborane, sodium borohydride ($NaBH_4$), sodium cyanoborohydride, lithium triethylborohydride, lithium tri(sec-butyl)borohydride, potassium tri(sec-butyl)borohydride, diisobutylaluminum hydride, lithium aluminum hydride, sodium bis(2-methoxyethoxy) aluminum hydride, or tributyltin hydride, for example, can be used.

As a reaction solvent to be used for the reduction of the ketone group, an arbitrarily selected solvent can be used as long as the reduction proceeds. In the case of using a polar aprotic solvent as a reaction solvent in Reaction 1, it also is possible to use the solvent continuously.

The acetylation in Reaction 2 can be performed, for example, using acetic anhydride or acetyl chloride.

As a reaction solvent to be used for the acetylation, an arbitrarily selected solvent can be used as long as the acetylation proceeds. In the case of using a polar aprotic solvent as a reaction solvent in Reaction 1, it also is possible to use the solvent continuously.

Next, the diamine compound <d> represented by formula (6) is obtained by reducing, to a methylene group, the carbon atom (carbon atom to which an acetoxy group is bonded) at the 9-position in the fluorene skeleton of the compound <c> obtained through Reaction 2 and reducing, to amino groups, the nitro groups that are included in substituents derived from the compound <a> and bonded to each of the carbon atoms at the 2-position and the 7-position (Reaction 3).

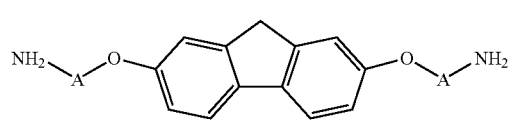

(6)

In Reaction 3, reductions may be performed, for example, by techniques such as hydrogenation, hydride reduction, and metal reduction. Reductants and/or catalysts to be used in the respective techniques may be the same as those used for the reduction of the ketone group in Reaction 2.

As a reaction solvent to be used for Reaction 3, an arbitrarily selected solvent can be used as long as Reaction 3 proceeds. In the case of using a polar aprotic solvent as a reaction solvent in Reaction 1, it also is possible to use the solvent continuously.

In Reaction 3, the reduction of the carbon atom at the 9-position and the reduction of the nitro groups may be performed simultaneously or separately.

Next, the diamine compound <d> obtained in Reaction 3 is subjected to a sulfonation reaction, so that a sulfonic acid group or a derivative thereof is introduced to each of the carbon atoms at the 3-position and the 6-position in the compound <d>. Thus, the sulfonic acid group-containing diamine compound of the present invention represented by formula (1) is obtained (Reaction 4).

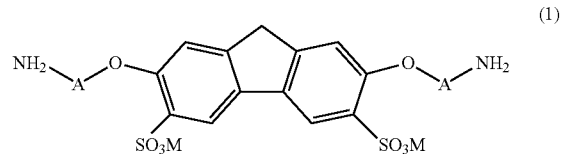

(1)

The sulfonating agent to be used for the sulfonation reaction in Reaction 4 is not particularly limited, as long as it allows sulfonic acid groups or derivatives thereof to be introduced to the aromatic rings in the fluorene skeleton of the compound <d>. Various sulfonating agents generally used can be used. Specific examples of the sulfonating agent include fuming sulfuric acid, sulfuric acid, sulfuric anhydride (sulfur trioxide), chlorosulfonic acid, 1,3,5-trimethylbenzene-2-sulfonic acid, 1,2,4,5-tetramethylbenzene-3-sulfonic acid, and 1,2,3,4,5-pentamethylbenzene-6-sulfonic acid. Particularly, fuming sulfuric acid, chlorosulfonic acid, and 1,3,5-trimethylbenzene-2-sulfonic acid are preferred, and fuming sulfuric acid is more preferred.

In Reaction 4, almost all the product to be obtained are a sulfonic acid group-containing diamine compound represented by formula (1) in which a sulfonic acid group or a derivative thereof is introduced to each of the carbon atoms at the 3-position and the 6-position, because the carbon atoms at the 2-position and the 7-position in the fluorene skeleton of the compound <d> each have an ether bond, which is electron donating.

Specific reaction conditions such as the reaction temperature and reaction time in Reactions 1 to 4 can be appropriately adjusted.

In the production method of the present invention, an optional reaction and optional step other than Reactions 1, 2, 3, and 4 may be performed, as needed. For example, in the case where the compound obtained in Reaction 4 is a compound represented by formula (12) below, a step of protecting the sulfonic acid group (—$SO_3H$) may be added after Reaction 4 in order to facilitate the handling of the compound. The sulfonic acid group, for example, is protected by converting the group into a salt (changing it into a salt of sulfonic acid group). Conversion into a salt can be performed, for example, by a reaction of the sulfonic acid group in formula (12) with a base.

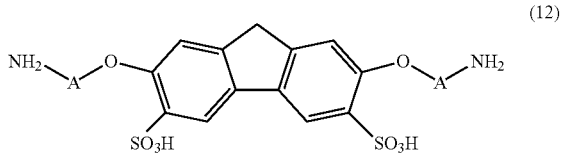

(12)

By the method described above, highly efficient synthesis of the sulfonic acid group-containing diamine compound of the present invention represented by formula (1) can be achieved, while the formation of by-products in which a substituent is bonded to the carbon atom at the 9-position is suppressed.

EXAMPLE

Hereinafter, the present invention is described further in detail with reference to the example. The present invention is not limited to the following example.

<Reaction 1>

100.0 g (471.3 mmol) of 2,7-dihydroxy-9-fluorenone, 146.3 g (1036.8 mmol) of 4-fluoronitrobenzene as the compound <a>, 260.5 g (1885.0 mmol) of potassium carbonate as a catalyst, and 1000 mL of N-methylpyrrolidone (NMP) as a reaction solvent were put in a four-necked separable flask with an internal volume of 2 L. Under stirring, the mixture in the flask was subjected to the reaction represented by formula (13) below in a nitrogen atmosphere at 90° C. for 3 hours. After the completion of the reaction, the contents in the flask were cooled to room temperature. Thereafter, they were poured into 10 L of ice water and precipitated crystal was collected by filtration. The collected crystal was washed sequentially with water and ethanol, followed by drying under reduced pressure. Thus, 197.4 g (yield rate: 92.2%) of the compound <b> shown on the right-hand side of formula (13) was obtained as an ocherous crystal. The compound <b> shown on the right-hand side of formula (13) is 2,7-bis(4-nitrophenoxy)-9-fluorenone.

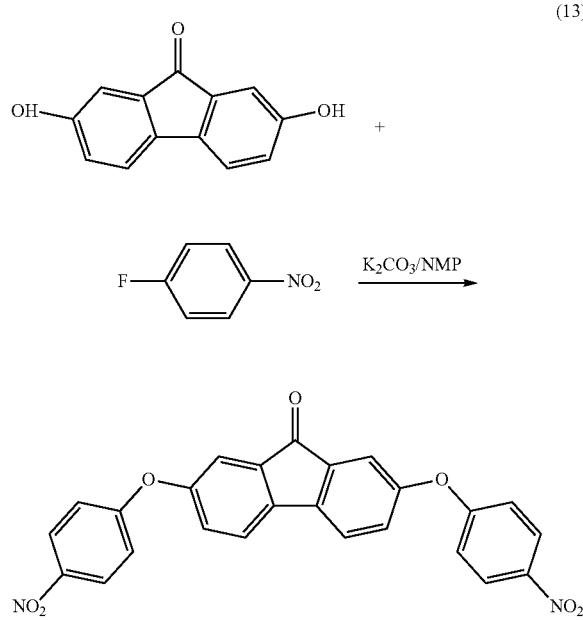

(13)

<Reaction 2>

150.0 g (330.1 mmol) of the compound <b> obtained by Reaction 1, 61.2 g (1617.6 mmol) of sodium borohydride and 123.3 g (924.3 mmol) of aluminum chloride (III) as a reductant, and 2.3 L of tetrahydrofuran (THF) as a reaction solvent were put into a four-necked separable flask with an internal volume of 3 L. The mixture in the flask was circulated in a nitrogen atmosphere for one night, so that the reaction represented by formula (14) below was allowed to proceed. Then, 1 L of water was added dropwise to the flask under cooling in an ice bath to cause quenching. Next, the reaction product was extracted with ethyl acetate and the extract was dried with sodium sulfate, which thereafter was concentrated under reduced pressure to undergo crystallization using heptane. Thus, 154.1 g (yield rate: 102.3%) of the compound shown on the right-hand side of formula (14) (2,7-bis(4-nitrophenoxy)-9-hydroxyfluorene) was obtained as a yellow crystal.

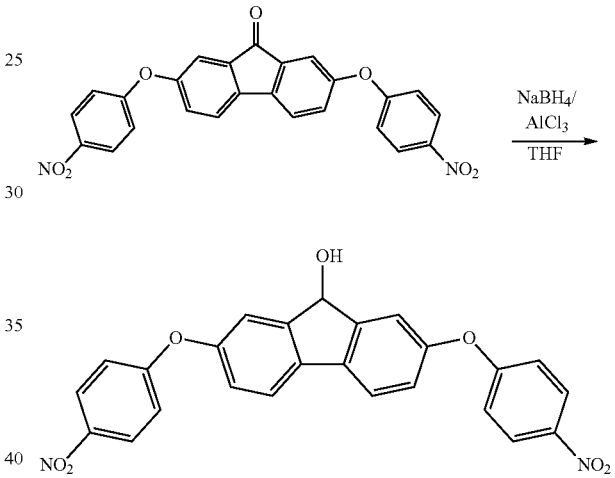

(14)

Next, 150.0 g (328.7 mmol) of the resultant compound, 2 L of dichloromethane, 39.9 g (394.4 mmol) of triethylamine, and 4.0 g (32.9 mmol) of N,N-dimethyl-4-aminopyridine (DMAP) were put into a four-necked separable flask with an internal volume of 3 L. The whole was cooled with ice, while a nitrogen atmosphere was maintained inside the flask. Then, 31.0 g (394.4 mmol) of acetyl chloride was added dropwise thereto, which was stirred for 3 hours. Thereafter, the temperature of the mixture in the flask was returned to room temperature and it was stirred for one night continuously, so that the reaction represented by formula (15) below was allowed to proceed. After the contents of the flask was poured into 3 L of ice water, the reaction product was extracted with dichloromethane and the extract was dried with sodium sulfate, which thereafter was concentrated under reduced pressure. The obtained residue was purified by column chromatography (silica gel: 1000 g; developing solvent: dichloromethane). The crystal thus obtained was crystallized using THF/heptane. Thus, 159.7 g (yield rate: 97.5%) of the compound <c> shown on the right-hand side of formula (15) was obtained as a pale orange crystal. The compound <c> shown on the right-hand side of formula (15) is 2,7-bis(4-nitrophenoxy)-9-acetoxyfluorene.

(15)

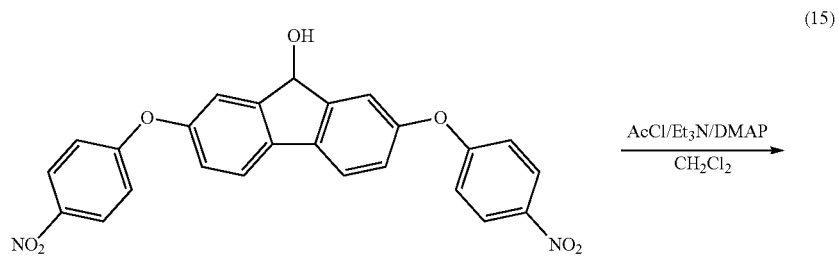

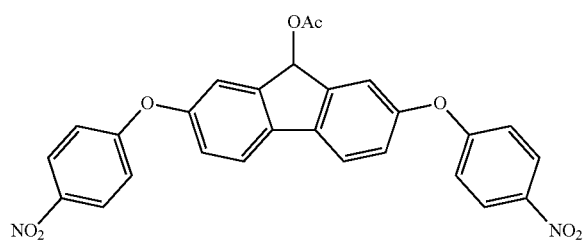

<Reaction 3>

159.0 g (319.0 mmol) of the compound <c> obtained by Reaction 2, 15.9 g of a 10-wt % palladium-activated carbon ethylenediamine complex as a reductant, and 3 L of THF as a reaction solvent were put into a four-necked separable flask with an internal volume of 5 L. The contents of the flask were stirred continuously at room temperature for 2 days while a hydrogen atmosphere was maintained inside the flask, so that the reaction represented by formula (16) below was allowed to proceed. After the completion of the reaction, the catalyst was removed from the contents of the flask by Celite filtration. Thereafter, the filtrate was concentrated under reduced pressure, which was crystallized using heptane. The crystallized crystal was further dissolved in a small amount of THF, which was crystallized using THF/ethanol. Thus, 101.1 g (yield rate: 83.3%) of the compound <d> shown on the right-hand side of formula (16) was obtained as a white crystal. The compound <d> shown on the right-hand side of formula (16) is 2,7-bis(4-aminophenoxy)fluorene (BAPF).

(16)

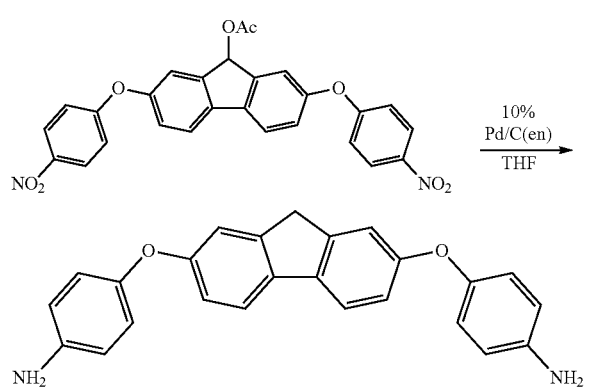

<Reaction 4>

47.6 g (125.0 mmol) of the compound <d> obtained in Reaction 3 and 100 mL of concentrated sulfuric acid were put into a four-necked separable flask with an internal volume of 2 L, and the compound <d> was dissolved therein by increasing the temperature up to 50° C., while the mixture in the flask was stirred. After the dissolution, the whole was cooled with ice to 0° C. Then, 17.5 mL of fuming sulfuric acid with a content of sulfur trioxide of 60 wt % was added dropwise into the flask gradually, while the contents in the flask was stirred. The cooling with ice was continued until 30 minutes had elapsed after the completion of the dropwise addition. Thereafter, the temperature of the contents in the flask was increased, and stirring at 50° C. was continued for 2 hours. Thus, the reaction represented by the following formula (17) was allowed to proceed. After the completion of the reaction, the reaction solution was cooled to room temperature, which was poured into 500 mL of ice water. Then, a precipitated solid product in the aqueous solution was separated by suction filtration. The separated solid product was dissolved in 1 L of a sodium hydroxide aqueous solution with a concentration of 1N, and impurities were removed by Celite filtration. While the resultant filtrate was stirred, concentrated hydrochloric acid was gradually added dropwise thereto so as to make the liquidity of the solution weakly acidic. Thus, a white solid product was precipitated. This solid product was subjected to suction filtration, and the separated solid product was washed with distilled water, which was again subjected to suction filtration. The separated solid product was washed with methanol, and was thereafter subjected to suction filtration. The separated solid product was dried under reduced pressure at 90° C. for 12 hours, thereby allowing 55.0 g (yield rate: 81.4%) of 2,7-bis(4-aminophenoxy)fluorene-3,6-disulfonic acid (BAPFDS) shown on the right-hand side of formula (17) to be obtained as a white crystal.

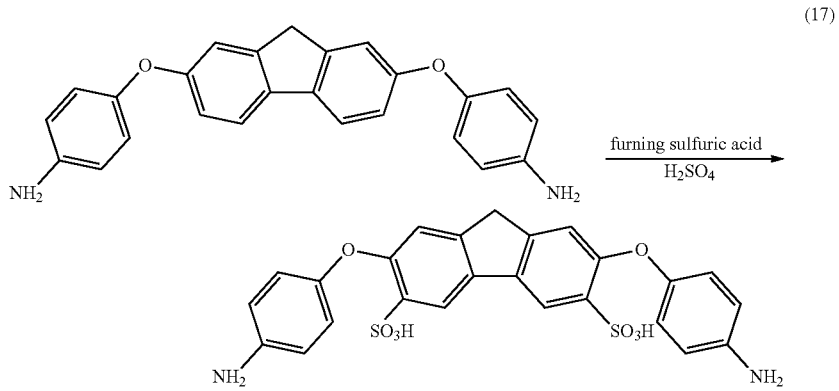

(17)

Figure 2:
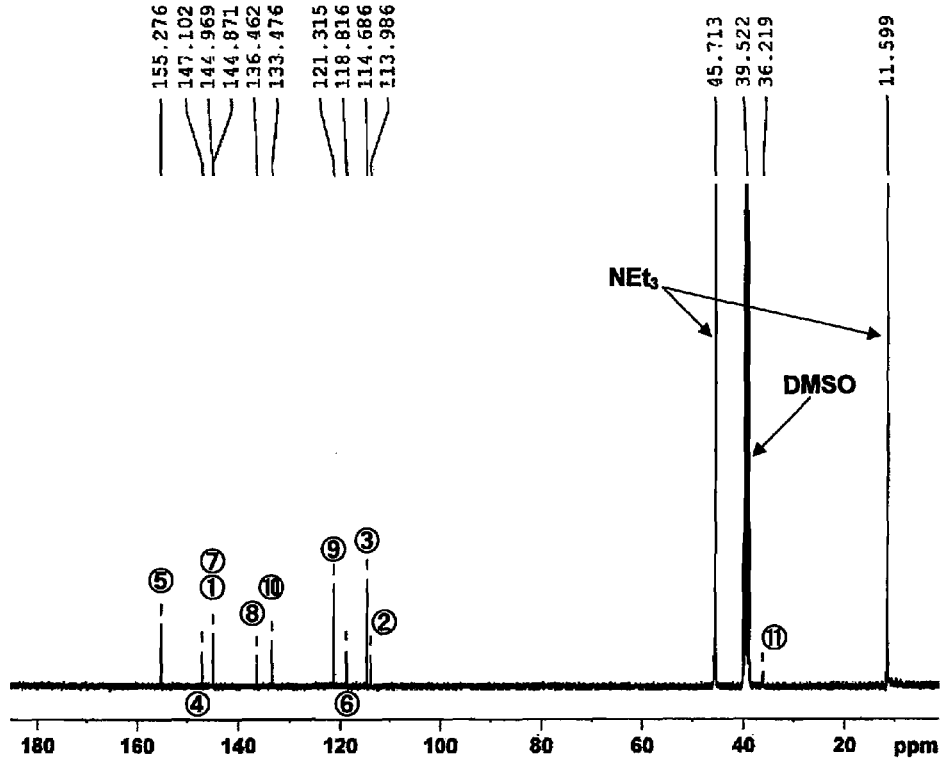
FIG. 2 is a graph showing a result of the carbon nuclear magnetic resonance spectroscopy ($^{13}$C-NMR) of 2,7-bis(4-aminophenoxy)fluorene-3,6-disulfonic acid synthesized in the example.

The obtained 2,7-bis(4-aminophenoxy)fluorene-3,6-disulfonic acid (BAPFDS) was identified by the $^1$H-NMR and $^{13}$C-NMR measurements (frequency: 300 MHz; solvent for measurements: dimethylsulfoxide-d6 (DMSO-d6)) using a nuclear magnetic resonance spectrometer (AVANCE II 300, manufactured by Bruker BioSpin Corporation). Since the BAPFDS was insoluble as it is in DMSO-d6, a small amount of triethylamine (NEt$_3$) was added thereto, thereby allowing a sulfonic acid group in the BAPFDS to change into triethyl ammonium salt of sulfonic acid group so as to be soluble in the DMSO-d6. The triethyl ammonium salt of BAPFDS thus obtained was subjected to various NMR measurements. The obtained $^1$H-NMR spectrum and $^{13}$C-NMR spectrum are respectively shown in FIGS. 1 and 2. Further, attribution of these spectra is shown below. As shown in FIGS. 1 and 2, peaks in the spectra were attributed to 6 types of hydrogen atoms and 11 types of carbon atoms in the BAPFDS.

$^1$H-NMR (300 MHz, DMSO-d6, δ in ppm)

3.665 (2H, CH$_2$), 4.883 (4H, NH$_2$), 6.555-6.576 (4H, CH), 6.744-6.766 (6H, CH), 8.040 (2H, CH)

$^{13}$C-NMR (300 MHz, DMSO-d6, δ in ppm)

36.219 (CH$_2$), 113.986 (CH), 114.686 (CH), 118.816 (CH), 121.315 (CH), 133.476 (C—S), 136.462 (C=C), 144.871-144.969 (C—N, C=C), 147.102 (C—O), 155.276 (C—O)

The present invention may be embodied in other forms without departing from the spirit or essential characteristics thereof. The embodiments described in this specification are to be considered in all respects only as illustrative and not restrictive. The scope of the invention is, therefore, indicated by the appended claims rather than by the foregoing description. All changes which come within the meaning and range of equivalency of the claims are to be embraced within their scope.

INDUSTRIAL APPLICABILITY

The sulfonic acid group-containing diamine compound of the present invention can be used in the same applications as for conventional sulfonic acid group-containing diamine compounds. The applications, for example, are a crosslinking agent or a raw material for thermosetting polymers or polycondensation polymers such as polyamide, polyimide, epoxy resin, and polyurethane.

The invention claimed is:

1. A sulfonic acid group-containing diamine compound represented by formula (1) below:

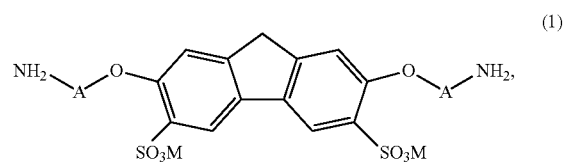

where
a group represented by [—SO$_3$M] is a sulfonic acid group, a salt of sulfonic acid group, or an ester of sulfonic acid group, A in a partial structure represented by [—O-A-NH$_2$] denotes:
a divalent aliphatic group R$^1$ which may have a substituent and has a carbon number of 1 to 10;
a divalent aromatic group Ar$^1$ which has 1 to 4 ring structures and may have a substituent;
a group represented by formula: [—Ar$^2$—Z$^1$—Ar$^3$—] (where Ar$^2$ and Ar$^3$, which may be the same as or different from each other, each are a divalent aromatic group which has 1 to 4 ring structures and may have a substituent, and Z$^1$ is a direct bond (—), an ether group (—O—), a thioether group (—S—), or a sulfone group (—SO$_2$—));
a group represented by formula: [—R$^2$—Ar$^4$—] (where R$^2$ is a divalent aliphatic group which may have a substituent and has a carbon number of 1 to 10, and Ar$^4$ is a divalent aromatic group which has 1 to 4 ring structures and may have a substituent); or
a group represented by formula: [—Ar$^5$—R$^3$—Ar$^6$—] (where Ar$^5$ and Ar$^6$, which may be the same as or different from each other, each are a divalent aromatic group which has 1 to 4 ring structures and may have a substituent, and R$^3$ is a divalent aliphatic group which may have a substituent and has a carbon number of 1 to 10), and the substituent which the aliphatic groups R$^1$, R$^2$, and R$^3$, and the aromatic groups Ar$^1$, Ar$^2$, Ar$^3$, Ar$^4$, Ar$^5$, and Ar$^6$ may have is at least one selected from a methyl group, an ethyl group, a propyl group, a butyl group, a trifluoromethyl group, a phenyl group, a phenoxy group, a phenylthio group, and a benzenesulfonyl group.

2. A method for producing the sulfonic acid group-containing diamine compound according to claim 1, comprising:

a step of obtaining a compound <b> represented by formula (4) by a condensation reaction of 2,7-dihydroxy-9-fluorenone represented by formula (2) and a compound <a> represented by formula (3):

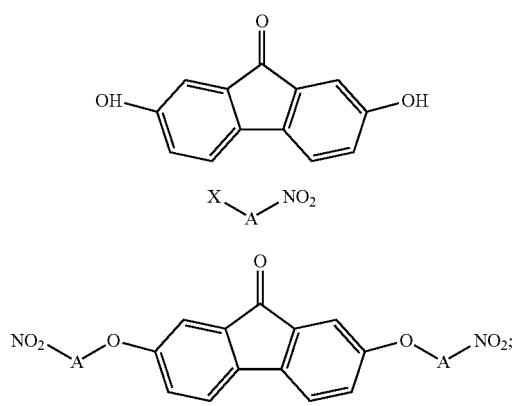

a step of obtaining a compound <c> represented by formula (5) by reducing a ketone group at the 9-position in a fluorene skeleton of the compound <b> to a state where a hydroxy group is bonded to a carbon atom at the 9-position and thereafter acetylating the hydroxy group:

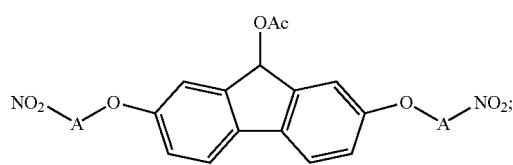

a step of obtaining a diamine compound <d> represented by formula (6) by reducing the carbon atom at the 9-position, to which the acetoxy group is bonded, in the fluorene skeleton of the compound <c> and reducing nitro groups that are included in the substituents derived from the compound <a> and bonded to carbon atoms at the 2-position and the 7-position in the skeleton:

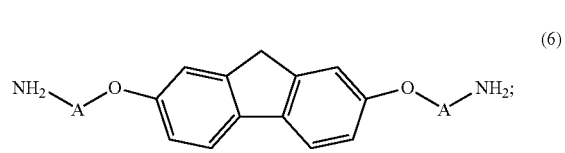

and a step of obtaining a sulfonic acid group-containing diamine compound represented by formula (1) in which a sulfonic acid group a salt of a sulfonic acid group or an ester of sulfonic acid group is introduced to each of the carbon atoms at the 3-position and the 6-position in the fluorene skeleton by subjecting the compound <d> to a sulfonation reaction:

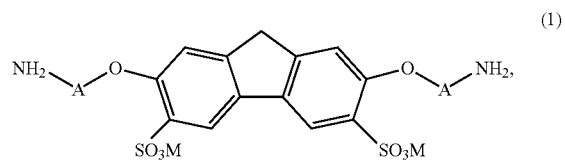

where
X in formula (3) is a halogen group, and
A in formulae (3) to (6) is the same group as A in the partial structure represented by [—O-A-NH$_2$] of the sulfonic acid group-containing diamine compound represented by the formula (1).

* * * * *